(12) United States Patent
Callaghan et al.

(10) Patent No.: US 11,700,868 B2
(45) Date of Patent: Jul. 18, 2023

(54) PRODUCT AND METHOD FOR PROVIDING ENRICHMENT AND FACILITATING EXPRESSION OF NATURAL BEHAVIORS IN PIGS

(71) Applicant: AUSTRALASIAN PORK RESEARCH INSTITUTE LTD, South Australia (AU)

(72) Inventors: Matthew John Callaghan, Toowong (AU); Robert John Van Barneveld, Manly (AU)

(73) Assignee: AUSTRALASIAN PORK RESEARCH INSTITUTE LTD, South Australia (AU)

( * ) Notice: Subject to any disclaimer, the term of this patent is extended or adjusted under 35 U.S.C. 154(b) by 246 days.

(21) Appl. No.: 17/243,207

(22) Filed: Apr. 28, 2021

(65) Prior Publication Data

US 2021/0345646 A1 Nov. 11, 2021

Related U.S. Application Data

(62) Division of application No. 15/545,156, filed as application No. PCT/AU2016/050036 on Jan. 22, 2016, now Pat. No. 11,129,396.

(30) Foreign Application Priority Data

Jan. 23, 2015 (AU) .................................. 2015900203

(51) Int. Cl.
| | | |
|---|---|---|
| *A23K 50/30* | (2016.01) | |
| *A23K 10/33* | (2016.01) | |
| *A23K 20/158* | (2016.01) | |
| *A23K 10/30* | (2016.01) | |
| *A23K 20/22* | (2016.01) | |
| *A01K 29/00* | (2006.01) | |
| *A01K 5/00* | (2006.01) | |
| *A61K 9/00* | (2006.01) | |
| *A61K 33/00* | (2006.01) | |
| *A61K 36/18* | (2006.01) | |
| *A61K 36/31* | (2006.01) | |
| *A01K 1/02* | (2006.01) | |

(52) U.S. Cl.
CPC ............... *A23K 50/30* (2016.05); *A01K 5/00* (2013.01); *A01K 29/005* (2013.01); *A23K 10/30* (2016.05); *A23K 10/33* (2016.05); *A23K 20/158* (2016.05); *A23K 20/22* (2016.05); *A61K 9/0056* (2013.01); *A61K 33/00* (2013.01); *A61K 36/18* (2013.01); *A61K 36/31* (2013.01); *A01K 1/0209* (2013.01); *A01K 1/0218* (2013.01); *Y02P 60/87* (2015.11)

(58) Field of Classification Search
CPC ........ A23K 50/30; A23K 10/30; A23K 10/33; A23K 20/158; A23K 20/22; A61K 9/0056; A61K 33/00; A61K 36/18; A61K 36/31; A01K 1/0209
See application file for complete search history.

(56) References Cited

U.S. PATENT DOCUMENTS

| | | | |
|---|---|---|---|
| 3,246,336 A | 4/1966 | Baribo et al. | |
| 3,532,503 A | 10/1970 | Kviesitis | |
| 4,027,043 A | 5/1977 | Schroeder et al. | |
| 4,171,385 A | 10/1979 | Skoch et al. | |

FOREIGN PATENT DOCUMENTS

| | | |
|---|---|---|
| AU | 1999045931 A1 | 4/2001 |
| CA | 1126568 A | 6/1982 |
| CN | 101176507 A | 5/2008 |
| CN | 104206812 A | 12/2014 |
| KR | 20110033684 A | 3/2011 |
| WO | WO 2001/01790 A1 | 1/2001 |
| WO | WO 2010/124869 A1 | 11/2010 |

OTHER PUBLICATIONS

Curtain "Molasses—General Considerations", excerpted from Molasses in Animal Nutrition (1983).
Diaz et al., "Studies on the Cell Wall Digestibility in Pigs Fed Leucaena (leucaena leucophala (Lam.) de Wit) Leaf Meal", *Journal of Animal and Veterinary Advances* 6:1190-1193 (2007).
Ellis, "Salt Tolerance and Salt Poisoning of Swine", Yearbook of Agriculture 803-809 (1942).
Feedipedia—soybean meal 2018.
Guthrie et al., "Roughage Source and Level in Beef Cattle Finishing Diets", *The Professional Animal Scientist* 12(3):192-198 (1996).
International Search Report and Written Opinion corresponding to International Patent Application No. PCT/AU2016/050036, dated Mar. 30, 2016, 9 pages.
Kallabis et al., "Effect of a high-fibre diet on the feeding behaviour of fattening pigs", *Archiv Tierzucht* 55:272-284 (2012).
Lammers "Feedstuffs for Pigs" (2007).
Naatjes, et al., "Energy requirement of growing pigs under commercial housing conditions", *Archives of Animal Nutrition* 68(2):93-110 (2014).
Phuc et al., "A molasses in diets for growing pigs", *Livestock Research for Rural Development* 5(2), 5 pages (Sep. 1993).
Saha et al., "Common terms used in animal feeding and nutrition", Bulletin 1367 of the University of Georgia (Mar. 2017).
Smith, "Salt: an essential element", *Angus Journal* Feb. 2008 Edition, pp. 177-179.
Zhu et al., "Poured feed blocks using distillery by-products as supplements for ruminants", *Journal of the Science of Food and Agriculture* 54:535-547 (1991).

(Continued)

*Primary Examiner* — Mina Haghighatian
*Assistant Examiner* — Nathan W Schlientz
(74) *Attorney, Agent, or Firm* — Brian C. Trinque; Lathrop GPM LLP

(57) ABSTRACT

The present invention relates to a formulation that can be utilised to facilitate expression of natural behaviour in pigs, and in particular sows and weaners and a method which utilises the formulation for the same.

16 Claims, 9 Drawing Sheets

(56) References Cited

OTHER PUBLICATIONS

Budino et al., "Behavior and performance of sows fed different levels of fiber and reared in individual cages or collective pens", *Annals of the Brazilian Academy of Sciences* 86(4):2109-2119 (2014).
De Leeuw et al., "Effects of dietary fibre on behaviour and satiety in pigs", *Proceedings of the Nutrition Society* 67(4):334-342 (2008).
Karamitros, "Sugar Beet Molasses for Growing and Fattening Pigs", *Animal Feed Science and Technology* 18(2):131-142 (1987).
Muller et al., "Use of a nutritional lick block and higher feeding levels to reduce aggression and provide enrichment for sows in groups", *Animal Production Science* 55(12):1498 (2015), URL:https://www.publish.csiro.au/AN/fulltext/ANv55n12Ab111.
Newberry, "Environmental enrichment: Increasing the biological relevance of captive environments", *Applied Animal Behaviour Science* 44:229-243 (1995).
Summons to Attend Oral Proceedings for European Application No. 16739691.0 dated Jan. 24, 2023, 12 pages.
Willett et al., "Cane Molasses for Pigs from Weaning to a Weight of Seventy Pounds", University of Hawaii, Agricultural Experiment Station, Technical Bulletin No. 3, pp. 1-15, Oct. 1946.
U.S. Appl. No. 15/545,156 / 2018-0000129 A1 / U.S. Pat. No. 11,129,396, filed Jul. 20, 2017 / Jan. 4, 2018 / Sep. 28, 2021, Matthew John Callaghan.
U.S. Appl. No. 17/243,207 / 2021-0345646 A1, filed Apr. 28, 2021 / Nov. 11, 2021, Matthew John Callaghan.

PRODUCT AND METHOD FOR PROVIDING ENRICHMENT AND FACILITATING EXPRESSION OF NATURAL BEHAVIORS IN PIGS

CROSS REFERENCE TO RELATED APPLICATIONS

This application is a divisional patent application of U.S. patent application Ser. No. 15/545,156, filed on Jul. 20, 2017, which application is a 35 U.S.C. § 371 filing of International Application No. PCT/AU2016/050036, filed on Jan. 22, 2016, which claims priority to Australian Patent Application No. 2015900203, filed on Jan. 23, 2015, the contents of each of which are incorporated herein by reference in their entirety.

FIELD OF THE INVENTION

The present invention relates to a formulation that can be utilised to facilitate expression of natural behaviour in pigs, and in particular sows and weaners and a method which utilises the formulation for the same.

BACKGROUND

In modern systems of animal production, pigs are often confined within simple, invariant, housing systems that offer little potential to accommodate their highly motivated species-specific behaviours. The thwarting of motivated behaviour can result in psychological distress and is associated with the manifestation of abnormal behaviours.

The welfare of pigs housed in intensive production systems is often viewed as being compromised. In contrast to the environments in which the pig has evolved, intensive production systems are often very barren with concrete (slatted) floors and no substrate in which the pigs can move around. Such environments thwart the expression of key behaviours such as exploration and foraging, which are highly motivated behavioural systems in the pigs. As a consequence, harmful aggressive behaviours often occur at high frequencies.

One example of harmful behaviours is found in the practice of mixing unfamiliar sows where the inability of sows to exhibit natural behaviour manifests into inter-sow aggression. The sows which are unfamiliar with each other will often fight when housed intensively in an unfamiliar or confined barren space, sometimes causing injury and lameness which in turn leads to economic loss. Furthermore, it is well known that piglets begin fighting within hours of birth and when pigs of any age meet. This is a consequence of separation from the dam, moving to a new environment and mixing with unacquainted younglings.

Environmental enrichment is the modification of a barren captive-environment to improve the biological functioning of pigs. Enriched environments enhance the well-being of animals by allowing them to perform more of their species-specific behavioural repertoire and accommodate a larger range of behavioural choices. Within the pig-production industry, a trade-off exists between the needs of the animals and that of the farming system in which they are reared. Producers have both economic and practical constraints on the extent to which they can offer environmental enrichment to their animals.

In one example for combating harmful behaviours in pigs, clinical experts in Europe have sought to use psychotropic or neuroleptic drugs as mentioned in Dantzer T., *Veterinary Science Communications* (1977) 1 pp 161-169. Examples of some drugs used were amperazide, chlorpromazine, azaperone, haloperidol, properciazine, prochlorperazine, diazepam, meprobamate, phenobarbital, phenothiazines and butyrophenones. However, no one knows the long-term effects of these drugs when humans consume meat taken from animals that have been given various drugs. In many cases, the administration of neuroleptic drugs in the feeds do not improve production and have further adverse effects such as slower weight increase and delayed sexual maturity (see Dantzer, supra).

Another example for combating harmful behaviours in pigs is described by Pageat (U.S. Pat. No. 6,384,252 B1) where a composition is provided comprising a mixture of fatty acids derived from secretions of mammalian mammary glands. Solutions of this composition were sprayed on the flat surfaces of surroundings for piglets, dogs, calves, lambs and children. In each instance, the treated surroundings resulted in the test subjects eating more food and appearing more relaxed. Unfortunately, the solution needed to be reapplied at the same time daily.

Another example for combating harmful behaviours in pigs is to address the lack of satiety associated with normal feeding. A modern sow diet during gestation consists of a restricted amount of feed delivered in one or two daily feeds. Diets are consumed within minutes not providing satiety and allowing feeding motivation to remain high. This prevents pigs from expressing their natural behaviour and accentuates inter-sow aggression in group housing. Nutritional satiety is commonly achieved through higher feeding levels. Unfortunately, this results in higher costs and adverse effects on reproduction and pig longevity. Thus what is needed is the development of a method which facilitates expression of natural behaviour in pigs which, for instance may reduce fighting amongst unfamiliar pigs. Ideally, any such method should not increase overall costs or management of the animal feed. This method would ideally: (1) increase species-specific behaviour; (2) maintain or improve levels of pig health; and (3) be practical to employ.

SUMMARY OF INVENTION

One aspect of the invention provides a feed composition comprising of molasses, insoluble fibre, triglyceride oil and salt for the improvement of the welfare in pigs. In an embodiment, the composition comprises a setting agent or combination thereof, and is preferably presented to the pigs as a solid or semi-solid composition. In an embodiment, the composition is presented as a solid form. In an embodiment, the solid form composition is achieved with the use of consumable food hardening agents. In an embodiment, the solid composition is presented as a block composition. In yet another aspect of the invention, the block composition further comprises soluble fibre. In yet another aspect of the invention, the composition is for the reduction of aggression in pigs.

One aspect of the invention is to provide a method to improve the welfare of pigs.

One aspect of the invention provides a feed composition comprising of molasses, insoluble fibre, triglyceride oil and salt to enhance environmental enrichment. A further aspect of the invention is to achieve environmental enrichment through nutrition. In an embodiment, the composition comprises a setting agent or combination thereof, and is preferably presented to the pigs as a solid or semi-solid composition. In an embodiment, the composition is presented as a solid form. In an embodiment, the solid form composition is achieved with the use of consumable food hardening agents. In an embodiment, the solid composition is presented as a block composition. In yet another aspect of the invention, the block composition further comprises soluble fibre.

One aspect of the invention is to provide a method which enhances pigs' environmental enrichment, and in particular the enrichment of pigs which are housed in intensive production systems.

The invention also provides a process for improving the welfare of pigs, said process comprising the step of providing to a pig a composition comprising of molasses, insoluble fibre, triglyceride oil and salt.

The invention also provides a process for enhancing environmental enrichment for a population of pigs housed in intensive production systems, said process comprising the step of providing to said population of pigs a composition comprising of molasses, insoluble fibre, triglyceride oil and salt.

DETAILED DESCRIPTION OF THE PREFERRED EMBODIMENTS

Figure 1:
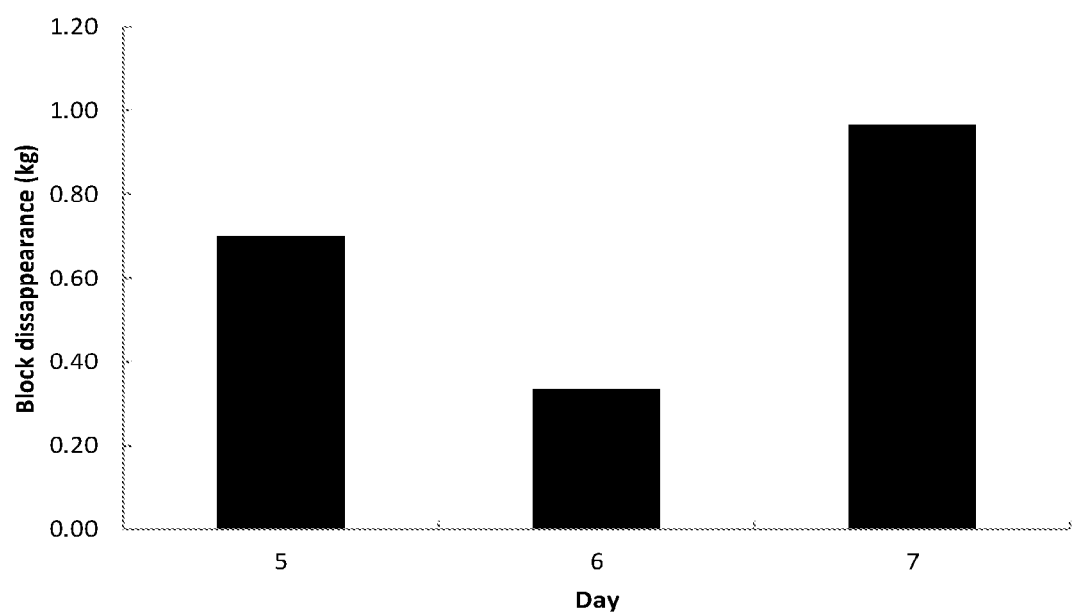
FIG. 1 depicts the mean daily disappearance (in kilograms) of the supplemental block, weighed over the 4 day observation period. Days 1-3 are non-experimental where the sows are held in individual stalls. Day 4 is the day of mixing and commencement of observations. Daily observations are conducted on days 5-7.

Pigs are motivated to explore novel stimuli of little biological value. It has been found that pigs reared in barren environments (such as intensive production systems) have elevated levels of exploratory motivation in comparison to pigs reared in enriched environments. Hence, as used herein, "improving the welfare of pigs" ensures that pigs have access to sufficient quantity of material to enable proper investigation and manipulation activities wherein said material does not compromise the health of the pigs. In order to make a determination of the welfare of pigs, the following parameters may be considered: object-directed behaviour, pen-directed behaviour, tail and ear biting, aggression, harmful social behaviour, activity, fear, production, health and hygiene.

As used herein, "environmental enrichment" is the modification of a barren captive-environment to improve the biological functioning of animals. Enriched environments enhance the well-being of animals by allowing them to perform more of their species-specific behavioural repertoire and accommodate a larger range of behavioural choices. Enriched environments result in pigs performing less frequent scampering and sparring behaviour. The typical classes of enrichment materials are metal objects, rubber, rope, wood, mineral blocks, roughage, substrates, straw and compound materials.

As used herein, "molasses" may be molasses obtained from a sugar mill (or be a by-product of molasses fermentation). The molasses can be any sugar-containing molasses such as cane or blackstrap molasses, beet molasses, converted molasses, wood sugar molasses, hydro syrup, citrus molasses or the like.

As used herein, "insoluble fibre" comprises pulp from crop plants such as maize, sorghum, wheat, sunflower, tomato, crucifers, peppers, potato, cotton, rice, soybean or soybean meal, sugar beet or beet pulp, sugarcane, tobacco, barley, oilseed rape.

As used herein, "soluble fibre" comprises galactomannan, glucomannan, pectin, arabinoxylan, cellulose, alginate or chitosan. Preferred are natural fibres. Natural fibres are expected not to hamper ingestion. In an embodiment, the fibres mentioned herein as alginate, galactomannans, glucomannans and pectin. These fibres have gelling properties. In another embodiment, the soluble fibres may be alginate, galactomannans or glucomannans. In an embodiment, the soluble fibre used is galactomannas. Galactomannan may be obtained by using beans from the group of *Vicia faba* (broad beans, known in the US as fava beans), *Vigna Aconitifolia* (Moth bean), *Vigna Angularis* (azuki bean), *Vigna mungo* (urad bean), *Vigna radiata* (mung bean), *Vigna umbellatta* (ricebean), *Vigna unguiculata* (cowpea—includes the black-eyed pea, yardlong bean and others), *Cicer arietinum* (chickpea also known as the garbanzo bean), *Pisum sativum* (pea), *Lathyrus sativus* (Indian pea), *Lathyrus tuberosus* (Tuberous pea), *Lens culinaris* (lentil), *Lablab purpureus* (hyacinth bean), *Phaseolus acutifolius* (tepary bean), *Phaseolus coccineus* (runner bean), *Phaseolus lunatus* (lima bean), *Phaseolus vulgaris* (common bean, includes the pinto bean, kidney bean, caparrones, and many others), *Glycine max* (soybean), *Psophocarpus tetragonolobus* (winged bean), *Cajanus cajan* (pigeon pea), *Stizolobium spp* (velvet bean), *Cyamopsis tetragonoloba* (guar), *Canavalia ensiformis* (jack bean), *Canavalia gladiata* (sword bean), *Macrotyloma uniflorum* (horse gram), *Lupinus mutabilis* (tarwi), *Lupinus albus* (lupini bean), and/or *Erythrina herbacea* (Coral bean).

As used herein, "triglyceride oil" comprises aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shark liver oil, shea nut oil, soybean oil, sunflower oil, tea seed oil, tobacco seed oil, vermonia oil, vegetable oil or wheat germ oil.

As used herein, "salt" is a term well known in the art and includes edible salts such as sodium chloride, sodium nitrite and the like. The salt in the present invention may restrict the upper levels of intake, promote water intake, induce satiety and provide additional nutrients. The salt may also act as a filler that may be replaced with other mineral sources such as magnesium salts, limestone or bentonite.

As used herein, "setting agents" comprises starches, agar, alginates, carrageenan, cellulose, pectin or gums such as guar gum, locust bean gum, Tara gum, Arabic gum, karaya gum and tragacanth gum.

As used herein, "hardening agents" comprise magnesium oxide, magnesium sulphate or any other food grade hardening agents such that in the required amounts the composition is presented in the form of a solid (such as a solid block) of required hardness.

One aspect of the invention is an enrichment program that is compatible with daily operations. A further aspect of the invention provides a cost effective, simple, effective and ongoing enrichment program compatible with management.

One aspect of the invention is the use of a poured supplemental block formulated for maximum attractiveness and hardness for longevity.

In specific embodiments, the molasses make up about 95% w/w or less, 90% w/w or less, 85% w/w or less, 80% w/w or less, 75% w/w or less, 70% w/w or less, 65% w/w or less, 60% w/w or less, 59% w/w or less, 58% w/w or less, 57% w/w or less, 56% w/w or less, 55% w/w or less, 54% w/w or less, 53% w/w or less, 52% w/w or less, 51% w/w or less, 50% w/w or less, 10% w/w or more, 15% w/w or more, 20% w/w or more, 25% w/w or more, 30% w/w or more, 35% w/w or more, 40% w/w or more, 45% w/w or more, 50% w/w or more, 55% w/w or more, 10% to about 90% w/w, 15% to about 85% w/w, 20% to about 80% w/w, 25% to about 75% w/w, 30% to about 70%, 35% to about 65% w/w, 40% to about 60%, 45% to about 55% of any composition described herein. In an embodiment, the molasses make up is from about 40% to about 70% w/w of the total composition, such as about 50% to about 60% w/w.

In specific embodiments, the insoluble fibre make up about 90% w/w or less, 80% w/w or less, 70% w/w or less, 60% w/w or less, 50% w/w or less, 40% w/w or less, 30% w/w or less, 20% w/w or less, 1% w/w or more, 2% w/w or more, 3% w/w or more, 4% w/w or more, 5% w/w or more, 6% w/w or more, 7% w/w or more, 9% w/w or more, 10% w/w or more, 11% w/w or more, 12% w/w or more, 13% w/w or more, 14% w/w or more, 15% w/w or more, 1% to about 90% w/w, 2% to about 80% w/w, 3% to about 70% w/w, 4% to about 60% w/w, 5% to about 50% w/w, 6% to about 40% w/w, 7% to about 30% w/w, 8% to about 20% w/w of any composition described herein. In an embodiment, the insoluble fibre makeup is about 10% to about 30% w/w of the total composition, such as about 10% to about 20% w/w.

In specific embodiments, the triglyceride oil make up is about 10% w/w or less, 9% w/w or less, 8% w/w or less, 7% w/w or less, 6% w/w or less, 5% w/w or less, 4% w/w or less, 3% w/w or less, 5% w/w or less, 0.1% w/w or more, 0.2% w/w or more, 0.3% w/w or more, 0.4% w/w or more, 0.5% w/w or more, 0.6% w/w or more, 0.7% w/w or more, 0.8% w/w or more, 0.9% w/w or more, 1% w/w or more, 0.1% to about 10% w/w, 0.2% to about 9% w/w, 0.3% to about 8% w/w, 0.4% to about 7% w/w, 0.5% to about 6% w/w, 0.6% to about 5% w/w, 0.7% to about 4% w/w, 0.8% to about 3% w/w, 0.9% to about 2% w/w, 1% to about 2% w/w of any composition described herein. In an embodiment, the triglyceride oil make up is about 1% to about 5% w/w of the total composition, such as about 1% to about 3% w/w.

In specific embodiments, the salt make up is about 20% w/w or less, 19% w/w or less, 18% w/w or less, 17% w/w or less, 16% w/w or less, 15% w/w or less, 14% w/w or less, 13% w/w or less, 12% w/w or less, 11% w/w or less, 10% w/w or less, 9% w/w or less, 8% w/w or less, 7% w/w or less, 6% w/w or less, 5% w/w or less, 0.5% w/w or more, 1% w/w or more, 1.5% w/w or more, 2% w/w or more, 2.5% w/w or more, 3% w/w or more, 3.5% w/w or more, 4% w/w or more, 4.5% w/w or more, 0.5% to about 20% w/w, 1% to about 19% w/w, 1.5% to about 18% w/w, 2% to about 17% w/w, 2.5% to about 16% w/w, 3% to about 15% w/w, 3.5% to about 14% w/w, 4% to about 13% w/w, 4% to about 12% w/w, 4% to about 11% w/w, 4% to about 10% w/w, 4% to about 9% w/w, 4% to about 8% w/w, 4% to about 7% w/w, 4% to about 6% w/w of any composition described herein. In an embodiment, the salt make up is about 2% to about 10% w/w of the total composition, such as about 3% to about 5% w/w or up to about 10% w/w.

In specific embodiments, the setting agents make about 90% w/w or less, 80% w/w or less, 70% w/w or less, 60% w/w or less, 50% w/w or less, 40% w/w or less, 30% w/w or less, 29% w/w or less, 28% w/w or less, 27% w/w or less, 26% w/w or less, 25% w/w or less, 2% w/w or more, 4% w/w or more, 6% w/w or more, 8% w/w or more, 10% w/w or more, 12% w/w or more, 14% w/w or more, 16% w/w or more, 2% to about 90% w/w, 4% to about 80% w/w, 6% to about 70% w/w, 8% to about 60% w/w, 10% to about 50% w/w, 12% to about 40% w/w, 14% to about 30% w/w, 16% to about 29% w/w, 16% to about 28% w/w, 16% to about 27% w/w, 16% to about 26% w/w, 16% to about 25% w/w, 16% to about 24% w/w, 16% to about 23% w/w, 16% to about 22% w/w of any composition described herein.

In specific embodiments, the soluble fibre make up about 20% w/w or less, 19% w/w or less, 18% w/w or less, 17% w/w or less, 16% w/w or less, 15% w/w or less, 14% w/w or less, 13% w/w or less, 12% w/w or less, 11% w/w or less, 10% w/w or less, 9% w/w or less, 8% w/w or less, 7% w/w or less, 6% w/w or less, 5% w/w or less, 0.5% w/w or more, 1% w/w or more, 1.5% w/w or more, 2% w/w or more, 2.5% w/w or more, 3% w/w or more, 3.5% w/w or more, 7% w/w or more, 4.5% w/w or more, 0.5% to about 20% w/w, 1% to about 19% w/w, 1.5% to about 18% w/w, 2% to about 17% w/w, 2.5% to about 16% w/w, 3% to about 15% w/w, 3.5% to about 14% w/w, 4% to about 13% w/w, 4% to about 12% w/w, 4% to about 11% w/w, 4% to about 10% w/w, 4% to about 9% w/w, 4% to about 8% w/w, 4% to about 7% w/w, 4% to about 6% w/w of any composition described herein.

In specific embodiments, the hardening agents make up is about 20% w/w or less, 19% w/w or less, 18% w/w or less, 17% w/w or less, 16% w/w or less, 15% w/w or less, 14% w/w or less, 13% w/w or less, 12% w/w or less, 11% w/w or less, 10% w/w or less, 9% w/w or less, 8% w/w or less, 7% w/w or less, 0.5% w/w or more, 1% w/w or more, 1.5% w/w or more, 2% w/w or more, 2.5% w/w or more, 3% w/w or more, 0.5% to about 20% w/w, 1% to about 19% w/w, 1.5% to about 18% w/w, 2% to about 17% w/w, 2.5% to about 16% w/w, 3% to about 15% w/w, 3% to about 14% w/w, 3% to about 13% w/w, 3% to about 12% w/w, 3% to about 11% w/w, 3% to about 10% w/w, 3% to about 9% w/w, 3% to about 8% w/w, 3% to about 7% w/w, of any composition described herein. In an embodiment, the hardening agents make up is about 2% to about 8% w/w of the total composition, such as about 3% to about 6.5% w/w.

In an embodiment, the composition comprises:
a) about 40% to about 70% w/w molasses;
b) about 10% to about 30% w/w insoluble fibre;
c) about 1% to about 5% w/w triglyceride oil; and
d) about 2% to about 10% w/w salt.

In a further embodiment, the composition comprises:
a) about 40% to about 70% w/w molasses;
b) about 10% to about 30% w/w insoluble fibre selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shark liver oil, shea nut oil, soybean oil, sunflower oil, tea seed oil, tobacco seed oil, vermonia oil, vegetable oil and wheat germ oil; and d) about 2% to about 10% w/w of salt selected from sodium chloride and sodium nitrite.

In a further embodiment, the composition comprises:
a) about 50% to about 60% w/w molasses;
b) about 10% to about 20% w/w insoluble fibre;
c) about 1% to about 3% w/w triglyceride oil; and
d) about 3% to about 5% w/w salt.

In a further embodiment, the composition comprises:
a) about 50% to about 60% w/w molasses;
b) about 10% to about 20% w/w insoluble fibre selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shark liver oil, shea nut oil, soybean oil, sunflower oil, tea seed oil, tobacco seed oil, vermonia oil, vegetable oil and wheat germ oil; and
d) about 3% to about 5% w/w of salt selected from sodium chloride and sodium nitrite.

In an embodiment, the composition comprises:
a) about 40% to about 70% w/w molasses;
b) about 10% to about 30% w/w insoluble fibre;
c) about 1% to about 5% w/w triglyceride oil;
d) about 2% to about 10% w/w salt; and
e) about 2% to about 8% w/w hardening agent.

In a further embodiment, the composition comprises:
a) about 40% to about 70% w/w molasses;
b) about 10% to about 30% w/w insoluble fibre selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shark liver oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite and;
e) about 2% to about 8% w/w hardening agent selected from magnesium oxide and magnesium sulphate.

In a further embodiment, the composition comprises:
a) about 50% to about 60% w/w molasses;
b) about 10% to about 20% w/w insoluble fibre;
c) about 1% to about 3% w/w triglyceride oil;
d) about 3% to about 5% w/w salt; and
e) about 3% to about 6.5% w/w hardening agent.

In a further embodiment, the composition comprises:
a) about 50% to about 60% w/w molasses;
b) about 10% to about 20% w/w insoluble fibre selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shark liver oil, shea nut oil, soybean oil, sunflower oil, tea seed oil, tobacco seed oil, vermonia oil, vegetable oil and wheat germ oil;
d) about 3% to about 5% w/w salt selected from sodium chloride and sodium nitrite; and
e) about 3% to about 6.5% w/w hardening agent selected from magnesium oxide and magnesium sulphate.

It has been found that an inclusion rate of 20% insoluble fibre into the diet resulted in an increase in lying behaviour and time taken to consume the meal. The fermentable fibre contained in this product is thought to delay the rate of passage of digesta and nutrient absorption and shift fermentation towards the hindgut. The shift to hindgut fermentation and improved gut health allows the proliferation of beneficial bacteria which produce high levels of volatile fatty acids ("VFA"). This VFA production may also impact satiety as it can play a role in stabilising blood glucose and insulin levels. The second dietary inclusion, the setting agent, has been suggested to play a role in insulin resistance. Stabilising insulin levels will in turn stabilise blood glucose levels, as insulin is a facilitator for circulating blood glucose through the bloodstream. Results also indicated that an inclusion rate of 0.1% of the setting agent, although not significant, increased overall lying behaviour.

As used herein, "aggression" may comprise either the approach of a dominant animal which invokes submission from another animal, a dominant animal aiming a blow to the head, neck or shoulder of another animal which may result in injury such as scratches on an animal's body.

An environmental enrichment program allows the animals' options or control over their environment and the option to employ behaviours which attain a desired outcome or endpoint (e.g. forage) or the information gathered through exploration. The use of a supplemental block provides opportunity for an enriched environment and elicits foraging behaviour in sows. Furthermore, the addition of a nutritional enrichment enables the addition of a satiety component to enhance chances of reducing aggression longer term. Furthermore, the provision of simple, cost-effective enrichment strategies greatly improves housing and welfare.

One aspect of the invention is to provide a method for improving the welfare of pigs. A further aspect of the invention is to provide a method to reduce aggression in pigs. A further aspect of the invention is to provide a method to reduce aggression in pigs by reducing chase behaviour. A further aspect of the invention is to provide a method to reduce aggression in pigs by causing adult pigs to spend less time foraging. A further aspect of the invention is to provide a method to reduce aggression in pigs by causing adult pigs to spend more time lying down.

One aspect of the invention is to provide a method to improve the welfare in adult pigs which comprises the following steps:
a) mixing adult pigs in a single pen;
b) providing the pigs of step a) a set amount of feed daily once or more times per day;
c) providing to the pigs a composition comprising of molasses, insoluble fibre, triglyceride oil and salt.

One aspect of the invention is to provide a method for the environmental enrichment of adult pigs which comprises the following steps:
a) mixing adult pigs in a single pen;
b) providing the pigs of step a) a set amount of feed daily once or more times per day;
c) providing to the pigs a composition comprising of molasses, insoluble fibre, triglyceride oil and salt.

A further aspect of the invention is to mix the adult pigs at a density of 5 $m^2$ or less, 4.5 $m^2$ or less, 4 $m^2$ or less, 3.5 $m^2$ or less, 3 $m^2$ or less, 2.5 $m^2$ or less, 2.4 $m^2$ or less, 2.3 $m^2$ or less, 2.2 $m^2$ or less, 2.1 $m^2$ or less, 2 $m^2$ or less, 1.9 $m^2$ or less, 0.5 $m^2$ or more, 0.6 $m^2$ or more, 0.7 $m^2$ or more, 0.8 $m^2$ or more, 0.9 $m^2$ or more, 1 $m^2$ or more, 1.2 $m^2$ or more, 1.4 $m^2$ or more, 1.6 $m^2$ or more, 0.5 to about 5 $m^2$, 0.6 to about 4.5 $m^2$, 0.7 to about 4 $m^2$, 0.8 to about 3.5 $m^2$, 0.9 to about 3 $m^2$, 1 to about 2.5 $m^2$, 1.2 to about 2 $m^2$, 1.4 to about 1.9 $m^2$ or 1.6 to about 1.9 $m^2$ per adult pig.

A further aspect of the invention is to provide about 5 kg or less, 4.5 kg or less, 4 kg or less, 3.5 kg or less, 3 kg or less, 2.9 kg or less, 2.8 kg or less, 2.7 kg or less, 2.6 kg or less, 2.5 kg or less, 2.4 kg or less, 1 kg or more, 1.5 kg or more, 2 kg or more, 1 to about 5 kg, 1 to about 4.5 kg, 1 to about 3.5 kg, 1.5 to about 3 kg, 1.5 to about 2.9 kg, 1.5 to about 2.8 kg, 1.5 to about 2.7 kg, 1.5 to about 2.6 kg, 1.5 to about 2.5 kg, 1.5 to about 2.4 kg of feed to each adult pig. As used herein, the term "feed" refers to commercially available feed. In one embodiment the commercially available feed is dry feed. In a further embodiment, the dry feed is grain based with plant protein additives such as canola or soybean meal. In a further embodiment, the dry feed may also contain a small percentage of highly concentrated protein additives such as meat, blood, bone or feather meals. In another embodiment, the commercially available feed is wet feed. In another embodiment, the commercially available feed is matched to the requirements of the animal. In another embodiment, the commercially available feed excludes a composition comprising of molasses, insoluble fibre, triglyceride oil and salt.

A further aspect of the invention is to provide 10 kg or less, 9 kg or less, 8 kg or less, 7 kg or less, 6 kg or less, 1 kg or more, 2 kg or more, 3 kg or more, 4 kg or more, 1 to about 10 kg, 1 to about 9 kg, 1 to about 8 kg, 2 to about 7 kg, 2 to about 6 kg of a composition comprising molasses, insoluble fibre, triglyceride oil and salt to each adult pig. As used herein, the terms "provide" or "providing" refer to animals being allowed to consume a composition comprising molasses, insoluble fibre, triglyceride oil and salt according to need. In one embodiment, the composition may be in the form of a liquid, slurry, semi-solid, granular or a solid. In a further embodiment, the composition may be housed in a lick wheel. In a further embodiment, the composition may be a feed block. Feed blocks may be manufactured by compressing ingredients into a moulded shape, by evaporative heating of the ingredients, by the setting of the ingredients into a shape or by gelation over several hours. In one embodiment, the shape of the feed block may take any shape. In a further embodiment, the shape of the feed block may have rounded faces. In a further embodiment, the shape of the feed block may have angular edges. Feed blocks offer the advantage of free choice to pigs thereby reducing the labour and expense otherwise incurred with multiple feeds. Feed blocks also offer the advantage of allowing the pig to express natural behaviours such as exploration, foraging, play and pushing the block around. Furthermore, once the composition is ingested, pig satiety is increased which results in a reduction of aggression.

One aspect of the invention is to improve the welfare of weaners. A further aspect of the invention is to provide a method to reduce aggression in weaners. A further aspect of the invention is to provide a method to reduce aggression in weaners by decreasing the time spent foraging. A further aspect of the invention is to provide a method to reduce aggression in pigs by decreasing the time spent nosing.

One aspect of the present invention is that the use of the composition as described above spans about 5 months or less, about 4 months or less, about 3 months or less, about 2 months or less, about 4 days or more, about 6 days or more, about 10 days or more, about 12 days or more, about 14 days or more, about 16 days or more, about 18 days or more, about 20 days or more, about 22 days or more or about 26 days or more. An advantage of the present invention is that the administration of the composition may cease after a suitable time period and pig producers may rely on just normal feed for the welfare of pigs. For instance, this will depend on the type of pig. For gestational sows, the administration of the composition may span the entire gestational period (5 months). This may have the advantage of reducing antagonistic behaviour around feeders prior to and immediately after feedings for sows in gestation. For weaner pigs, the administration of the composition may span from 1 day to 7 days. This may have the advantage of reducing antagonistic behaviour of weaners post-weaning. For adult pigs, the administration of the composition may span from 1 day to 14 days. This may have the advantage of reducing antagonistic behaviour.

One aspect of the invention is to provide a method to improve the welfare in weaners which comprises the following steps:
a) mixing the weaners in a single pen;
b) providing the weaners of step a) feed at least once a day;

c) providing to the weaners a composition comprising of molasses, insoluble fibre, triglyceride oil and salt.

One aspect of the invention is to provide a method for the environmental enrichment for weaners which comprises the following steps:
a) mixing the weaners in a single pen;
b) providing the weaners of step a) feed at least once a day;
c) providing to the weaners a composition comprising of molasses, insoluble fibre, triglyceride oil and salt.

A further aspect of the invention is to mix pigs, for instance weaner pigs, at a density of 3 m² or less, 2.5 m² or less, 2 m² or less, 1.5 m² or less, 1 m² or less, 0.9 m² or less, 0.8 m² or less, 0.7 m² or less, 0.6 m² or less, 0.5 m² or less, 0.4 m² or less, 0.3 m² or less, 0.05 m² or more, 0.1 m² or more, 0.15 m² or more, 0.2 m² or more, 0.21 m² or more, 0.22 m² or more, 0.23 m² or more, 0.24 m² or more, 0.25 m² or more, 0.05 to about 3 m², 0.1 to about 2.5 m², 0.15 to about 2 m², 0.15 to about 1.5 m², 0.2 to about 1 m², 0.2 to about 0.9 m², 0.2 to about 0.8 m², 0.2 to about 0.7 m² or 0.2 to about 0.6 m² per pig.

A further aspect of the invention is to provide about 5 kg or less, 4.5 kg or less, 4 kg or less, 3.5 kg or less, 3 kg or less, 2.9 kg or less, 2.8 kg or less, 2.7 kg or less, 2.6 kg or less, 2.5 kg or less, 2.4 kg or less, 2.3 kg or less, 2.2 kg or less, 2.1 kg or less, 2 kg or less, 1.75 kg or less, 1.5 kg or less, 1 kg or less, 0.8 kg or less, 0.6 kg or less, 0.4 kg or less, 0.2 kg or less, 0.05 kg or more, 0.10 kg or more, 0.20 kg or more, 0.5 kg or more 1.5 kg or more, 2 kg or more, 0.05 to about 5 kg, 0.05 to about 4 kg, 0.05 to about 3 kg, 0.05 to about 2 kg, 0.05 to about 1.5 kg, 0.05 to about 1 kg, 0.05 to about 0.75 kg, 0.05 to about 0.5 kg, 0.05 to about 0.25 kg, 1 to about 5 kg, 1 to about 4.5 kg, 1 to about 3.5 kg, 1.5 to about 3 kg, 1.5 to about 2.9 kg, 1.5 to about 2.8 kg, 1.5 to about 2.7 kg, 1.5 to about 2.6 kg, 1.5 to about 2.5 kg, 1.5 to about 2.4 kg of feed to each pig.

A further aspect of the invention is to provide 5 kg or less, 4 kg or less, 3 kg or less, 2 kg or less, 1.5 kg or less, 0.05 kg or more, 0.10 kg or more, 0.25 kg or more, 0.5 kg or more, 0.75 kg or more, 1 kg or more, 2 kg or more, 3 kg or more, 4 kg or more, 0.05 to about 5 kg, 0.05 to about 4 kg, 0.05 to about 3 kg, 0.05 to about 2 kg, 0.05 to about 1.5 kg, 0.05 to about 1 kg, 0.05 to about 0.75 kg, 0.05 to about 0.5 kg of a composition comprising molasses, insoluble fibre, triglyceride oil and salt to each pig.

A further aspect of the invention provides the composition in a solid form, wherein said composition has a hardness of 1 kg/cm² to 6 kg/cm². A further aspect of the invention provides the composition in a solid form to weaners, wherein said composition has a hardness of 2.5-3.0 kg/cm². A further aspect of the invention provides the composition in a solid form to sows, wherein said composition has a hardness of 4.0 kg/cm². Hardness may be measured by a soil penetrometer, with each block individually tested.

Control of hardness is important to achieve. Overly soft blocks will result in excessive consumption or product loss which is both economically and metabolically wasteful. However if blocks are too hard then consumption will be inadequate and animals will lose interest. The size of the animal is also an important consideration and large sows would generally be expected to consume much more than a 3-4 week old, naive piglet. It has been found that the hardness of the sow blocks appears appropriate for weaners at 10 weeks of age however consumption of the same block was inadequate by very young weaner pigs. Thus the weaner pig block has been designed at a lower target hardness. The hardness in the weaner blocks may be reduced by lowering concentrations of hardening agents and also by removing the blocks from the heat source at an earlier stage in the transition from a liquid slurry into a solidified form.

EXAMPLES

Data Collection and Analysis

Behavioural recordings consisted of pen video monitoring and recording during the 4 day observation period. Daily observations during this period began upon entry into the pen (0700 hours) and for a period of 1 hour after feeding. Behaviour and posture activity was recorded by scan sampling at 1 minute intervals at the playback of recorded videos. An ethogram was established for posture observations entailing standing, lying sternal and lying lateral as well as behavioural observations of block interaction, aggression and inactivity. Time spent engaged in push, chase, attack, bite and threat behaviours were considered aggressive behaviour.

Individual fresh scratches were counted at 0800 hours on days 2 and 4 of each experimental week, and were pooled to provide a scratch score per treatment group per day. Saliva samples were collected from each sow during each treatment period at three time periods; day 1 (baseline), day 4 at mixing and day 7, 3 days post mixing. The individual samples were then pooled on a treatment basis and analysed for cortisol as an indicator of the stress responseto mixing. Groups were stocked at a density of 1.8 m²/sow and fresh water made available ad libitum via a nipple drinker. All data was analysed using Genstat analysis of variance with treatment as the fixed factor and individual sow being a blocking factor.

Example 1—Preparation of Sample Blocks in a Laboratory

The block formulation was prepared comprising of insoluble fibre pulp, guar gum, salt, canola oil, molasses and setting agents. This formulation could be transported as a liquid until poured into moulds.

A steel rod is placed vertically through the block so that it can be attached in the pen. Approximately 100 mm of steel extends above and below the block. The inside of the container and lid was sprayed with canola oil. This allowed the block to slide out easily. The blocks were cured either at ambient temperature over 1-2 weeks or placed in a drying oven at 45-50° C. for 24 hours. A total of 21 blocks was made with the average block weight being approximately 1.2 kg (Table 1).

TABLE 1

Pig block Weights

| Block No. | Steel (g) | Container + Lid (g) | Poured wet block weight (g) |
|---|---|---|---|
| 1 | 733 | 73 | scale error - missed weight |
| 2 | 733 | 73 | 1204 |
| 3 | 732 | 73 | 1233 |
| 4 | 734 | 74 | 1237 |
| 5 | 733 | 73 | 1205 |
| 6 | 734 | 72 | 1225 |
| 7 | 732 | 73 | 1279 |
| 8 | 734 | 72 | 1215 |
| 9 | 733 | 63 | 1209 |
| 10 | 733 | 59 | 1208 |
| 11 | 733 | 72 | 1235 |
| 12 | 733 | 72 | 1205 |

TABLE 1-continued

Pig block Weights

| Block No. | Steel (g) | Container + Lid (g) | Poured wet block weight (g) |
|---|---|---|---|
| 13 | 733 | 71 | 1212 |
| 14 | 734 | 71 | 1217 |
| 15 | 734 | 69 | 1202 |
| 16 | 734 | 69 | 1236 |
| 17 | 734 | 74 | 1198 |
| 18 | 734 | 73 | 1217 |
| 19 | 732 | 73 | 1227 |
| 20 | 735 | 73 | 1245 |
| 21 | 733 | 72 | 1241 |

Example 2—Preparation of Sample Blocks in a Commercial Setting

The formulation for the block comprised molasses, vegetable oil, water, insoluble fibre pulp, salt and setting agents. The blocks produced in a commercial setting were approximately 12 kg by weight and made for sow trials.

Example 3—Preparation of Test Blocks for Use in Sow Trials

The formulation for the block comprised molasses, vegetable oil, water, sugar, insoluble fibre pulp, salt and setting agents. The blocks produced in a commercial setting were approximately 25-30 kg by weight. These were the blocks used in the following trials.

Example 4—the Use of Blocks in Sow Trials

This study was conducted at the Westbrook research facility and involved the following experimental groups:
Control: 2.3 kg/sow/day of dry sow diet, floor fed in two places at 0700 hours;
High feeding level (HFL): 4 kg/sow/day, floor fed at maximum dispersal (bag of diet spread around most of pen) at 0700 hours; and
Block enrichment (BE): 2.3 kg/sow/day, floor fed in two places at 0700 hrs. A 30 kg supplemental Block is placed in centre of pen (not fixed) on Day 1 and weighed daily.

Thirty-six non-reproductive sows and gilts were included in the study and allocated to the experimental groups where a cross over design was used to pseudo-randomise six multi-parous sows into one of the three treatment groups for six replicates (n=36). The experimental unit was the pen. Each experimental replicate ran for 7 days. During days 1-3, sows were housed in individual stalls and fed 2.3 kg per day. On day 4, sows were introduced into one of three treatment pens before 7.00 am for a 4-day observation period, as per treatment matrix (Table 2).

TABLE 2

Treatment structure for pseudo-randomised cross-over design to investigate the effects of high feeding level (High feed) or the use of a supplement block (Block) to reduce aggression in mixed sows compared to an untreated control (Control).

| Replicate | Treatment | Sow | | | | | |
|---|---|---|---|---|---|---|---|
| 1 | Control | 1 | 2 | 3 | 4 | 5 | 6 |
| | Block | 7 | 8 | 9 | 10 | 11 | 12 |
| | High feed | 13 | 14 | 15 | 16 | 17 | 18 |
| 2 | Control | 31 | 32 | 33 | 34 | 35 | 36 |
| | Block | 19 | 20 | 21 | 22 | 23 | 24 |
| | High feed | 25 | 26 | 27 | 28 | 29 | 30 |
| 3 | Control | 2 | 8 | 14 | 20 | 26 | 32 |
| | Block | 3 | 9 | 15 | 21 | 27 | 33 |
| | High feed | 1 | 7 | 13 | 19 | 36 | 31 |
| 4 | Control | 4 | 10 | 16 | 22 | 28 | 34 |
| | Block | 5 | 11 | 17 | 23 | 29 | 35 |
| | High feed | 6 | 12 | 18 | 24 | 30 | 25 |
| 5 | Control | 3 | 10 | 17 | 24 | 36 | 32 |
| | Block | 1 | 8 | 15 | 22 | 29 | 25 |
| | High feed | 2 | 9 | 16 | 23 | 30 | 31 |
| 6 | Control | 5 | 12 | 13 | 20 | 27 | 34 |
| | Block | 6 | 7 | 14 | 21 | 28 | 35 |
| | High feed | 4 | 11 | 18 | 19 | 26 | 33 |

After 4 days, sows were returned to individual stalls for the next replicate (3 days in individual stalls followed by 4 days in experimental treatment pens). This was repeated six times to obtain 6 replicates of each treatment. Daily data collection during the 4 day observation period involved; measurement of block weight, behavioural and posture observations, individual sow scratch scores to measure the prevalence of aggressive behaviour, and salivary cortisol samples. The block was weighed daily at 0700 hrs.

Behavioural Observations

A generalised linear model revealed that introducing the supplement block or feeding at a higher level of 4.0 kg/day resulted in significantly reduced chase behaviour (P<0.05, Table 3). The addition of the block and feeding at a higher level had a significant effect on posture, with sows on both these treatment groups spending less time standing, and a greater time spent lying (P<0.05) than the control group.

TABLE 3

Mean time (min) sows' spent engaged in behaviour and posture 1 h after feeding over the four days of observation, for sows in the control group and receiving 2.3 kg/day, sows receiving a high-feeding level (4.0 kg day) or sows receiving a supplement block in addition to 2.3 kg feed day.

| | Treatment | | | SED | P value |
|---|---|---|---|---|---|
| | Control | Block | High feed | | |
| | Activity | | | | |
| Push | 0.09 | 0.08 | 0.10 | 0.24 | 0.868 |
| Chase | $0.29^a$ | $0.08^b$ | $0.11^b$ | 0.47 | 0.019 |
| Attack | 0.40 | 0.42 | 0.36 | 0.58 | 0.811 |
| Bite | 0.10 | 0.12 | 0.06 | 0.25 | 0.392 |
| Threat | 0.13 | 0.11 | 0.10 | 0.27 | 0.736 |
| Sham-chewing | 0.62 | 0.51 | 0.39 | 0.82 | 0.257 |
| Foraging | $28.48^x$ | $25.67^{xy}$ | $25.15^y$ | 9.76 | 0.084 |
| Total aggression | 1.01 | 0.81 | 0.73 | 0.94 | 0.186 |
| | Posture | | | | |
| Lying | $9.13^b$ | $13.30^a$ | $13.66^a$ | 11.30 | 0.038 |
| Sitting | 0.24 | 0.79 | 0.88 | 1.67 | 0.114 |
| Standing | $50.63^a$ | $45.91^b$ | $45.26^b$ | 10.85 | 0.006 |

$^{ab}$Means in a row with different superscripts differ significantly (P < 0.05);
$^{xy}$Means in a row with different superscripts differ significantly (P < 0.10);
Control, offered 2.3 kg/d; Block, offered 2.3 kg/d and a 30 kg block; High feed, offered 4 kg/d; SED, standard error of difference of the means; Total aggression, combined time spent in push, chase, attack, bite and threat behaviours.

Across all experimental treatments, the mean length of time spent engaged in a fight significantly decreasing after the first day (P<0.05, Table 4). Posture showed a similar response to fighting with significantly reduced time spent standing in the days after mixing, with more time spent sitting, and in particularly lying.

TABLE 4

Mean time (min) sows' spent engaged in behaviour and posture 1 h after feeding, for all treatments over the 4 days of behavioural monitoring during the 4-day observation period.

| | Day | | | | | |
|---|---|---|---|---|---|---|
| | 4 | 5 | 6 | 7 | SED | P value |
| Activity | | | | | | |
| Push | 0.14 | 0.06 | 0.06 | 0.09 | 0.28 | 0.291 |
| Chase | 0.07 | 0.11 | 0.22 | 0.19 | 0.55 | 0.192 |
| Attack | 0.57 | 0.34 | 0.32 | 0.35 | 0.67 | 0.107 |
| Bite | 0.09 | 0.13 | 0.06 | 0.10 | 0.20 | 0.351 |
| Threat | 0.07 | 0.11 | 0.15 | 0.13 | 0.30 | 0.381 |
| Fight time (s) | $9.67^a$ | $3.44^b$ | $3.38^b$ | $2.56^b$ | 6.39 | <0.001 |
| Sham-chewing | 0.52 | 0.54 | 0.43 | 0.55 | 1.15 | 0.920 |
| Foraging | 27.23 | 24.80 | 27.02 | 26.67 | 11.57 | 0.578 |
| Total aggression | 0.94 | 0.76 | 0.80 | 0.92 | 1.10 | 0.716 |
| Posture | | | | | | |
| Lying | $6.48^b$ | $13.30^a$ | $14.47^a$ | $14.12^a$ | 11.19 | <0.001 |
| Sitting | 0.15 | 0.58 | 0.76 | 0.96 | 2.13 | 0.264 |
| Standing | $53.37^a$ | $46.12^b$ | $44.77^b$ | $44.92^b$ | 11.93 | <0.001 |

$^{ab}$Means in a row with different superscripts differ significantly (P < 0.05);
SED, standard error of difference of the means; Day, days 1-3 non-experimental held in individual stalls, day 4, day of mixing and commencement of daily observations (days 5, 6 and 7); Fight time, mean length of fighting bout; Total aggression, combined time spent in push, chase, attack, bite and threat behaviours.

Behavioural observations of sow interaction with the supplement block were monitored and there were no aggressive interactions associated with the block or with sows around the block. Previous work established an ethogram of block interaction also lacked block associated aggression and inter-sow interaction around the block at any given time.

Salivary Cortisol and Scratch Injuries

TABLE 5

Mean levels of salivary cortisol (µg/dl) taken on Day 1 and considered the baseline sample; Day 4, (day of mixing) and Day 7 (4 d post mixing for sows) in the control group and receiving 2.3 kg/day, sows receiving a high-feeding level (4.0 kg day) or sows receiving a supplement block in addition to 2.3 kg feed/day.

| | Treatment | | | | |
|---|---|---|---|---|---|
| Sample | Control | Block | High feed | SED | P value |
| Day 1 | 0.50 | 0.38 | 0.47 | 0.06 | 0.219 |
| Day 4 | 0.47 | 0.85 | 0.40 | 0.20 | 0.104 |
| Day 7 | 0.63 | 0.93 | 0.54 | 0.23 | 0.268 |

SED, standard error of difference of the means

TABLE 6

Mean number of fresh scratch injuries scored on Day 5, (one day after mixing) and day 7 (4 d post mixing) of sows in the control group and receiving 2.3 kg/day, sows receiving a high-feeding level (4.0 kg day) or sows receiving a supplement block in addition to 2.3 kg feed/day.

| | Treatment | | | | |
|---|---|---|---|---|---|
| | Control | Block | High feed | SED | P value |
| Day 5 | 6.8 | 10.0 | 8.8 | 3.40 | 0.653 |
| Day 7 | 4.8 | 7.3 | 5.0 | 2.76 | 0.614 |

SED, standard error of difference of the means

Further analysis revealed that days tended to have a significant effect (P=0.078) on the mean number of fresh scratch injuries with the mean number of fresh scratch injuries counted decreasing from Day 5 (one day after mixing) to day 7 (4 days after mixing) (Table 7).

TABLE 7

Mean number of fresh scratch injuries scored on Day 5, one day after mixing and Day 7, the final experimental day across all treatments.

| | Day | | | |
|---|---|---|---|---|
| | 5 | 7 | SED | P value |
| Scratch Injuries | $8.56^x$ | $5.72^y$ | 1.61 | 0.078 |

$^{xy}$Means in a row with different superscripts differ significantly (P < 0.10);
SED, standard error of difference of the means The supplemental block was weighed at 3 time periods over the 4-day observation period, results showed a mean disappearance of 2 kg during this time (FIG. 1).

Example 5—the Use of Blocks in Weaner Trials

Figure 4:
FIG. 4 depicts one embodiment of the use of 1.2 kg blocks in weaner trials as defined in the process according to the present invention.
Figure 5:
FIG. 5 depicts one embodiment of the use of 1.2 kg blocks in weaner trials as defined in the process according to the present invention.
Figure 6:
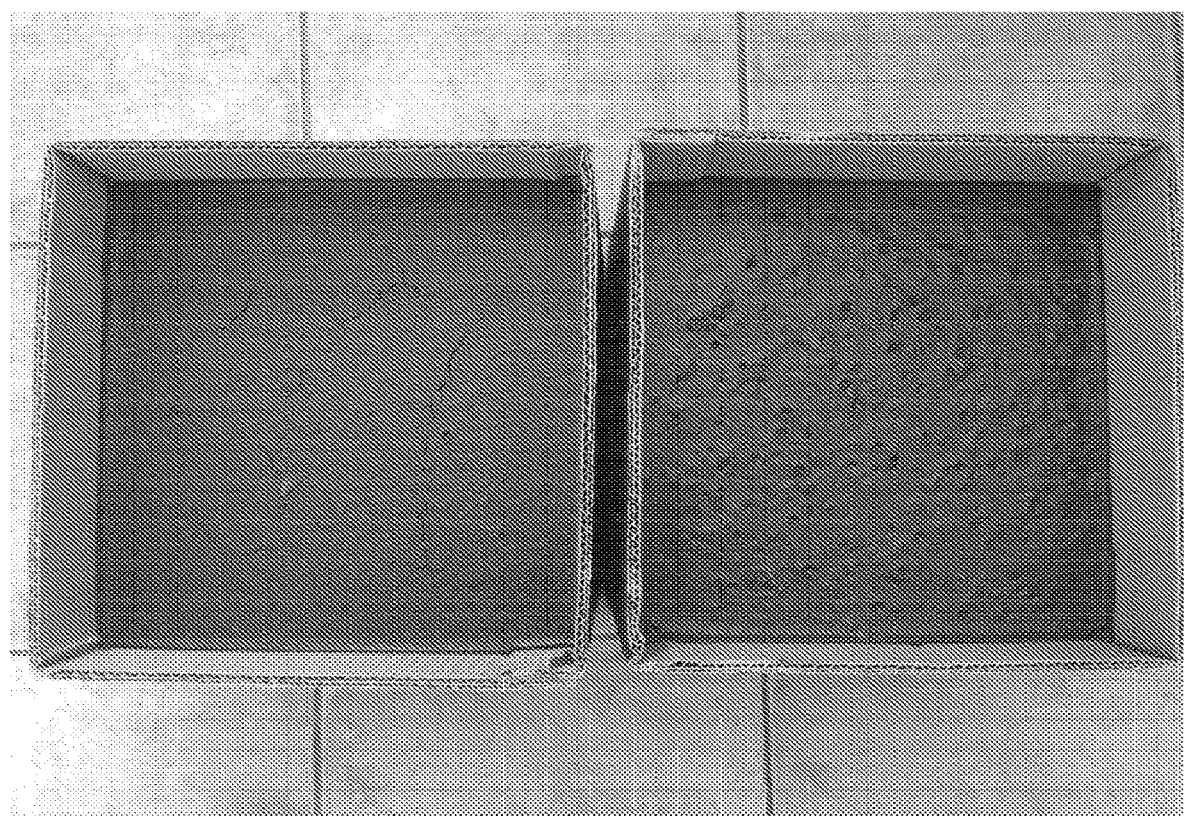
FIG. 6 depicts one embodiment of the blocks as defined in the block composition according to the present invention. The blocks depicted are approximately 15 kg.
Figure 7:
FIG. 7 depicts one embodiment of the process as defined according to the present invention.

This experiment investigated the use of a supplemental block to provide enrichment to newly mixed weaner pigs (7 weeks old). The ingredients included within the block were aimed to induce satiety through the addition of a fibre-rich by-product in a molasses and salt base. The block was centrally fitted with a steel bar to enable attachment to the pen. This was done using a metal chain threaded through the centre of the bar and attached with a d-link fitting around the anterior fence of the pen (FIGS. 4 and 5).

Weaner pigs were housed in pens (1 m×2.8 m) with open galvanized panelling and fully slatted plastic floor tiles. Water was supplied ad libitum via two nipple drinkers and supplementary radiant heat was provided via a bar heater. Feed was offered ad libitum to each pen via a round multi-space adjustable plastic transit feeder. Feed intake and block disappearance was calculated from feed offered and block weight on day 1 and weighed refusal and block weight after 24 hrs of observations, day 2.

A randomised block design, blocked by sex and weight, was used to randomly allocate 20 weaners into one of two treatment pens, replicated six times. The experimental unit was the pen and the experimental groups were:
Control: weaners mixed into a barren pen
Block: weaners mixed into a pen fitted with a 1.2 kg supplemental block Observations Behavioural recordings consisted of pen video monitoring for 24 hours after mixing. Observations consisted of scan sampling at 1 minute intervals for the $1^{st}$ hour and recording only fighting bouts thereafter for 23 hours. Fighting bouts over the 23 hour time period were condensed and scored as taking place during 1 of 5 time periods. Time spent engaged in push, chase, fight and bite behaviours were considered aggressive behaviour. Nosing behaviour was considered pen-directed behaviour and compared against total time spent at the block. Fresh scratch injuries were counted after 24 hours of observation and pooled to provide a scratch score per treatment group.

Observed behavioural parameters were grouped into three categories, postures, aggression and pen-directed behaviour, and expressed as the mean relative number of 1 minute intervals of occurrences. Data was analysed using Univariate General Linear Model (Genstat v15.0 VSN International, Hemel Hempstead, UK) to examine the effects of treatment on time spent displaying aggressive and exploratory behaviour and postures.

In order to meet requirements of normally distributed data, data was checked for normality. Period, the effect of time, was a blocking factor for treatment effects. Scratch injuries were pooled at a pen level and analysed using the same model. Differences were determined by least significant difference (P<0.05).

Outcomes

TABLE 8

Mean time (min) weaner pigs spent engaged in behaviour and posture during 1 h after mixing, for weaner pigs in the control group and housed in barren pen or weaner pigs receiving a supplemental block in an enriched pen.

| | Treatment | | | |
|---|---|---|---|---|
| | Control | Block | SED | P value |
| Activity | | | | |
| Push | 0.28 | 0.30 | 0.08 | 0.856 |
| Chase | 0.25 | 0.25 | 0.63 | 1.000 |
| Bite | 0.68 | 0.40 | 0.20 | 0.217 |
| Fight | 1.25 | 0.90 | 0.26 | 0.247 |
| Total aggression | 2.47 | 1.85 | 0.33 | 0.124 |
| Posture | | | | |
| Lying | 25.9 | 17.9 | 4.49 | 0.137 |
| Standing | 34.1 | 42.1 | 4.49 | 0.137 |

Control, barren pen; Block, enriched pen with a 1.2 kg block; SED, standard error of difference of the means; Total aggression, combined time spent in push, chase, attack, bite and threat behaviours.

It was evident that weaner pigs mixed in a pen fitted with a supplemental block spent less time foraging (P<0.10) and nosing (P<0.05) than those housed in a barren pen (Table 9). Furthermore, a mean time of 18.05 min was spent at the block over a 60 min observational period, immediately after mixing.

TABLE 9

Mean time (min) weaner pigs spent engaged in foraging, pen-directed behaviour (nosing), and time spent at the block during 1 h after mixing, for weaner pigs in the control group and housed in barren pen or weaner pigs receiving a supplemental block in an enriched pen.

| | Treatment | | | |
|---|---|---|---|---|
| Activity | Control | Block | SED | P value |
| Nosing | 11.37 | 6.17 | 0.92 | 0.002 |
| Foraging | 17.2 | 8.80 | 0.43 | 0.058 |
| Time spent at block | 0 | 18.10 | 3.31 | <0.001 |

Control, barren pen; Block, enriched pen with a 1.2 kg block; Nosing, considered a pen-directed behaviour; SED, standard error of difference of the means.

Figure 2:
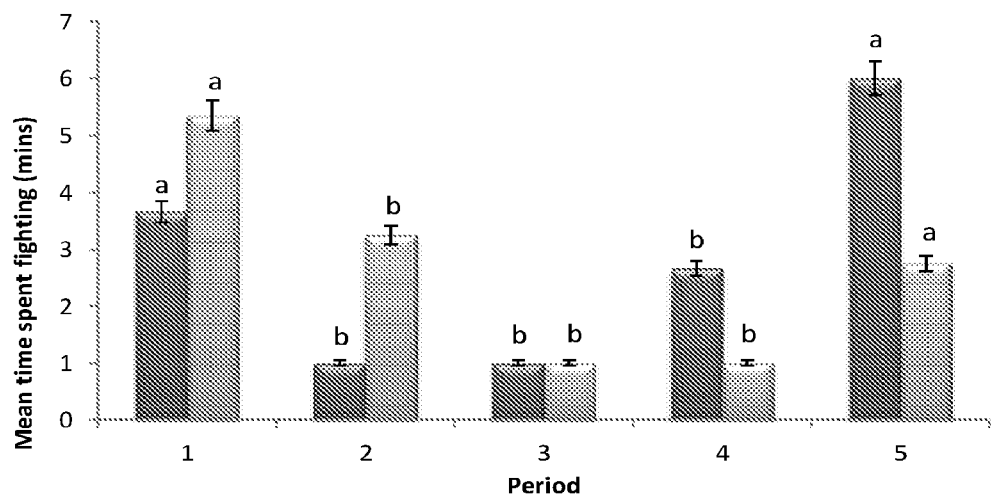
FIG. 2 depicts mean time (in minutes) where weaner pigs spent time engaged in fighting behaviour 23 hours after mixing. The information provided shows weaner pigs in the control group and housed in a barren pen (dark grey bars) and weaner pigs receiving a supplemental block in an enriched pen (light grey bars).

Fighting bouts were observed and counted for a 23 hour time period, 1 hour post mixing period and scored to have occurred during 1 of 5 time periods (FIG. 2);

period 1 at 4.5 hours;

period 2 at 4 hours;

period 3 at 4 hours;

period 4 at 5.5 hours; and period 5 at 5 hours.

TABLE 10

Mean number of fresh scratch injuries scored 24 hours after mixing of weaner pigs in the control group and housed in a barren pen or weaner pigs receiving a supplemental block in an enriched pen.

| | Treatment | | | |
|---|---|---|---|---|
| | Control | Block | SED | P value |
| Scratch Injuries | 35.8 | 35.2 | 8.37 | 0.940 |

SED, standard error of difference of the means

Figure 3:
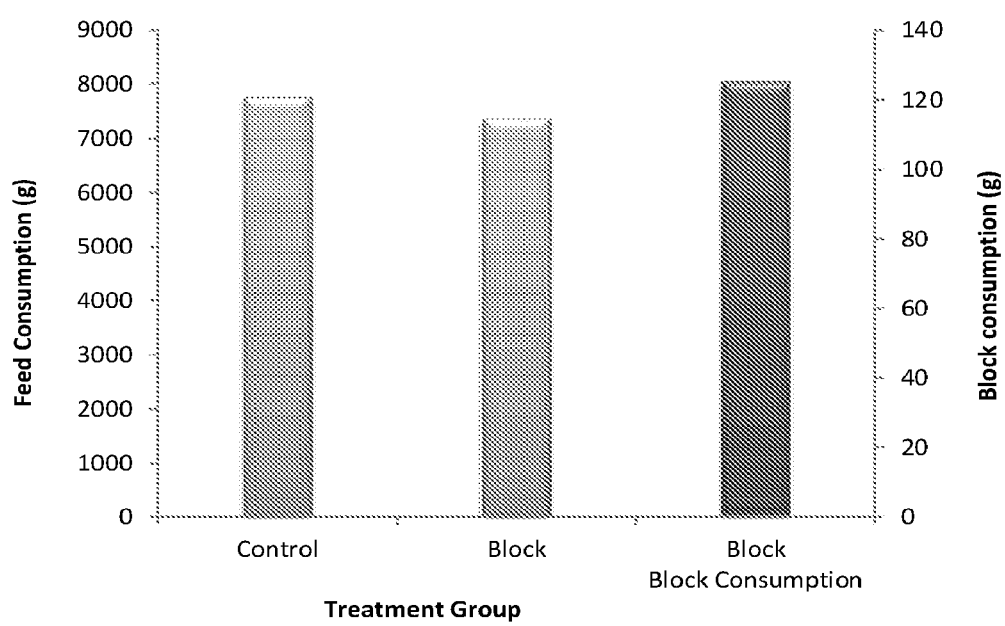
FIG. 3 depicts mean disappearance (in grams) of the supplemental block (dark grey bars) and feed intake (light grey bars) weighed after 24 hours of observation of weaner pigs in the control group and housed in barren pen and weaner pigs receiving a supplemental block in an enriched pen.

The block disappearance and feed intake was measured after the 24 hour observation period (FIG. 3). Results showed a mean block disappearance of 125 g/pen over the 24 hour observational period. Mean feed intake for the control group measured 7757 g and 7357 g for those pens fitted with the supplemental block over the 24 hour observational period.

Example 6—the Use of Blocks in Gestational Sow Trials

A standard gestation sow diet (14.5 MJ digestible energy (DE)/kg, 0.55 available lysine/MJ DE) was fed to all treatments in a randomised block design study. The block was formulated to include sugarbeet pulp (SBP) and Magnesium oxide (MgO), in a molasses and salt base. Groups of 15 multiparous sows were mixed immediately after mating and randomly allocated to one (1) of three (3) treatments. Each experimental treatment ran for four (4) days and was replicated 10 times with a new group of sows.

On day 0, unfamiliar sows were randomly mixed into 1 of 3 experimental treatment pens and floor fed 2.5 kg/sow/day at 7.15 am over a 4-day observational period. The experimental unit was the pen and the experimental treatment groups are:

Control: 2.5 kg/sow/day of dry sow diet, floor fed at 0715 hrs.

One Block: 2.5 kg/sow/day of dry sow diet, floor fed at 0715 hrs. A 20 kg supplemental block was placed in the pen (not fixed) on Day 0 and weighed daily.

Two Block: 2.5 kg/sow/day of dry sow diet, floor fed at 0715 hrs. Two 20 kg supplemental blocks were placed in opposite ends of the pen (not fixed) on Day 0 and weighed daily.

Daily data collection during the 4-day observational period involved measurement of block weight daily at 1000 hrs, individual scratch injury scores and behavioural and posture observations to measure the prevalence of aggressive behaviour associated with feeding.

Behavioural Observations

Behavioural recordings consisted of pen video monitoring and observations during the experimental period, beginning with a 45 min period immediately after feeding on Day 1 (Day after mixing, first day of group feeding; sows were mixed on day 0 without feeding) and Day 3 (3 days post mixing). Behaviour and posture activity was recorded by scan sampling at 1 min intervals at the playback of recorded videos, according to a standard ethogram (Table 11).

TABLE 11

Ethogram used for recording sow activity in a study to investigate the effects of the use of a supplement block.

| Postures | |
|---|---|
| Standing | Body supported by all four legs |
| Lying | Lying with chest and stomach flat on floor, head held up off the floor or lowered |
| Behaviours | |
| Fight | Two sows taking part in a violent struggle involving exchange of physical blows |
| Push | Using body to exert force on another sow |
| Chase | Movement of pursuit towards another sow using a fast paced continuous locomotion which displaces the sow |
| Attack | Forceful violent movement towards neighbor to initiate a fight |
| Bite | Use of teeth to grip another sow aggressively |
| Threat | Sudden head movement or move towards another sow which submitted or retreated without contact being made |
| Foraging | Eating or searching for substrate from ground to ingest or eat |
| Rooting | Thrusting nose into substrate (block) to move it around |
| Nosing | Rubbing substrate (block) with nose in a repetitive motion |

Time spent engaged in push, chase, attack, bite, threat and fight behaviours were considered agonistic behaviour. Time spent rooting and nosing were considered block interaction.

Fresh Scratch Injuries

A sub sample of sows (30%) was used to indicate an injury score, individual scratch injuries were counted on Days 1 and 3 after behaviour was recorded. Each side of the sow's body was divided into 21 areas and the number and type of skin injuries recorded. Skin injures were categorised into fresh injuries or partially healed or old injuries and pooled to give a pen total.

Block Weighing

Cardboard encasing the block, used for packaging and handling, was stripped off to eliminate weight changes contributing to absorption of moisture. Block weights were measured daily for the duration of the experiment or until complete disappearance.

Reproductive Success

Reproductive performance parameters will be assessed for all sows from herd records. Total born, stillborn, pigs born alive and pigs weaned will be analysed along with pre-weaning mortality.

Statistical Analysis

Observed behavioural parameters were grouped into two categories, postures and agonistic behaviours, and expressed as the mean relative number of 1 min intervals of occurrences. With pen being the experimental unit, pen totals were calculated from individual sow data and analysed for the effects of treatment, period and day, as well as interactions, using Unbalanced Univariate General Linear Model (Genstat v15.0 VSN International, Hemel Hempstead, UK) to examine the effects on time spent displaying agonistic behaviours and postures.

In order to meet requirements of normally distributed data, data was checked for normality. Replicate, the effect of time, and Day were blocking factors for treatment effects. Scratch injuries were pooled at a pen level and analysed using the same model. Differences were determined by least significant difference (P<0.05).

Behavioural Observations

There was a trend (P<0.10) for sows to spend more time standing in the 45 min period immediately after feeding with the addition of two supplement blocks (Table 12).

TABLE 12

Mean time (min) sows' spent engaged in behaviour and posture 45 min after feeding, on Days 1 and 3 of being newly mixed, for sows in the control group and receiving 2.5 kg/day, sows receiving a supplement block in addition to 2.5 kg feed/day or sows receiving two supplement blocks in addition to 2.5 kg feed/day.

| | Treatment | | | | |
|---|---|---|---|---|---|
| | Control | One block | Two blocks | SED | P value |
| Activity | | | | | |
| Push | 0.14 | 1.02 | 1.01 | 0.408 | 0.187 |
| Chase | 0.07 | 0.15 | 0.17 | 0.108 | 0.738 |
| Attack | 0.02 | 0.14 | 0.18 | 0.068 | 0.212 |
| Bite | 0.01 | 0.35 | 0.52 | 0.200 | 0.153 |
| Threat | $0.01^b$ | $0.21^a$ | $0.38^a$ | 0.102 | 0.011 |
| Fight | 0.28 | 0.64 | 0.47 | 0.226 | 0.430 |
| Block interaction | 0 | 0.22 | 0.42 | 0.272 | 0.178 |
| Foraging | 25.77 | 25.09 | 27.57 | 2.431 | 0.567 |
| Agonistic behaviour | 0.04 | 0.21 | 0.23 | 0.080 | 0.169 |
| Posture | | | | | |
| Lying | 9.88 | 11.16 | 7.72 | 1.712 | 0.136 |
| Standing | $35.00^{xy}$ | $33.51^y$ | $37.57^x$ | 1.650 | 0.086 |

$^{ab}$Means in a row with different superscripts differ significantly (P < 0.05);
$^{xy}$Means in a row with different superscripts differ significantly (P < 0.10);
Control, offered 2.5 kg/d; One Block, offered 2.5 kg/d and a 20 kg block; Two Blocks, offered 2.5 kg/d and 2 × 20 kg blocks; SED, standard error of difference of the means; Block interaction, combined time spent in rooting and nosing behaviours; Agonistic behaviour, is the combined time spent in push, chase, attack, bite, threat and fight behaviours.

Posture showed a significant response (P>0.05), with a reduced time spent lying, in the days after mixing, with more time spent standing and foraging (Table 13).

TABLE 13

Mean time (min) sows' spent engaged in behaviour and posture 45 min after feeding, for all treatments on Days 1 and 3 of mixing unfamiliar sows into a gestation pen.

| | Day | | | |
|---|---|---|---|---|
| | 1 | 3 | SED | P value |
| Activity | | | | |
| Push | 0.53 | 0.78 | 0.339 | 0.479 |
| Chase | 0.12 | 0.12 | 0.089 | 0.983 |
| Attack | 0.13 | 0.08 | 0.056 | 0.440 |
| Bite | 0.19 | 0.34 | 0.169 | 0.401 |
| Threat | 0.15 | 0.21 | 0.098 | 0.616 |
| Fight | 0.39 | 0.49 | 0.181 | 0.568 |
| Block interaction | 0.25 | 0.15 | 0.235 | 0.552 |
| Foraging | $22.29^b$ | $30.40^a$ | 1.938 | <0.001 |
| Agonistic behaviour | 0.13 | 0.17 | 0.066 | 0.541 |
| Posture | | | | |
| Lying | $11.33^a$ | $7.60^b$ | 1.438 | 0.015 |
| Standing | $33.49^b$ | $37.31^a$ | 1.413 | 0.012 |

$^{ab}$Means in a row with different superscripts differ significantly (P < 0.05);
SED, standard error of difference of the means; Day 1, day after mixing; Day 3, 3 days post mixing; Block interaction, combined time spent in rooting and nosing behaviours; Agonistic behaviour, is the combined time spent in push, chase, attack, bite, threat and fight behaviours.

Fresh Scratch Injuries

Although it was found that treatment had no significant effect on fresh scratch injuries on Day 1, there was a significant effect on Day 3 with the mean number of fresh scratch injuries being highest in the Control treatment groups compared to the One block and Two block treatment groups (P<0.05; Table 14).

TABLE 14

Mean number of fresh scratch injuries scored on Day 1, (day after mixing) and day 3 (3 d post mixing) of sows in the control group and receiving 2.5 kg/day, sows receiving a supplement block in addition to 2.5 kg feed/day or sows receiving two supplement blocks in addition to 2.5 kg feed/day.

| | Treatment | | | | |
|---|---|---|---|---|---|
| | Control | One block | Two Blocks | SED | P value |
| Day 1 | 8.34 | 8.70 | 8.28 | 0.781 | 0.845 |
| Day 3 | 1.70$^b$ | 1.10$^a$ | 0.96$^a$ | 0.304 | 0.038 |

$^{ab}$Means in a row with different superscripts differ significantly (P < 0.05);
SED, standard error of difference of the means Further analysis revealed that day tended to have a significant effect (P<0.001) on the mean number of fresh scratch injuries with injuries counted decreasing significantly from day 1 to day 3 (Table 15).

TABLE 15

Mean number of fresh scratch injuries scored on Day 1, day after mixing and Day 3, 3 days post mixing.

| | Day | | | |
|---|---|---|---|---|
| | 1 | 3 | SED | P value |
| Scratch Injuries | 8.44$^b$ | 1.25$^a$ | 0.363 | <0.001 |

Figure 8:
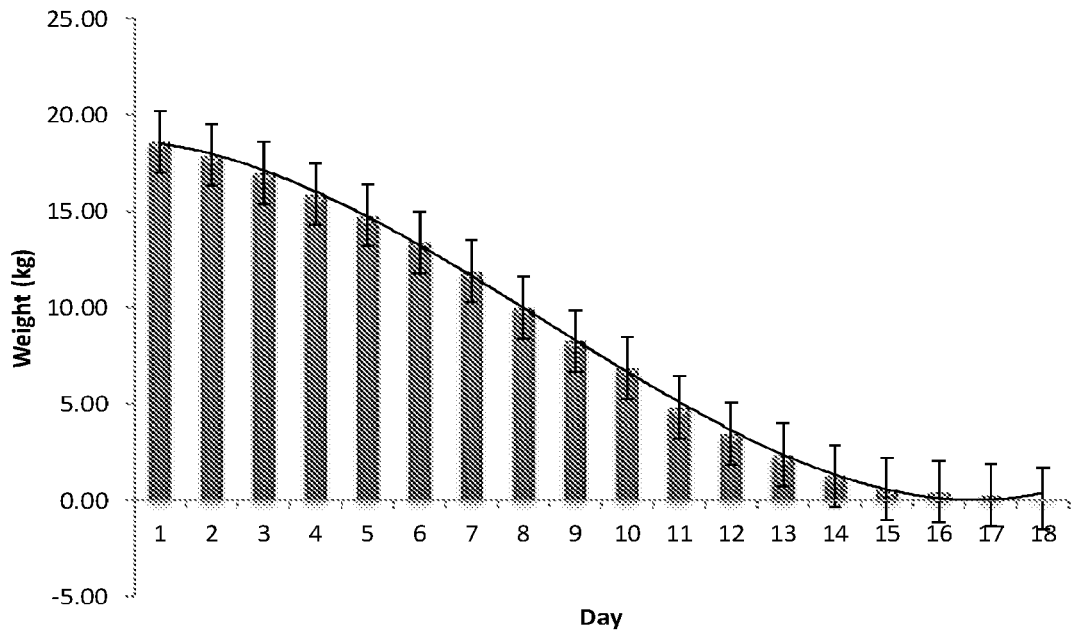
FIG. 8 depicts the mean block weight (kg) measured from day 1 of mixing unfamiliar sows into a group pen with either 1 or 2×20 kg block(s).

$^{ab}$Means in a row with different superscripts differ significantly (P < 0.05);
SED, standard error of difference of the means Block Weighing The supplement blocks were weighed daily until complete disappearance. Mean block weight remains stable for the initial days after mixing before a period of faster disappearance and levelling off at the end (FIG. 8).

Figure 9:
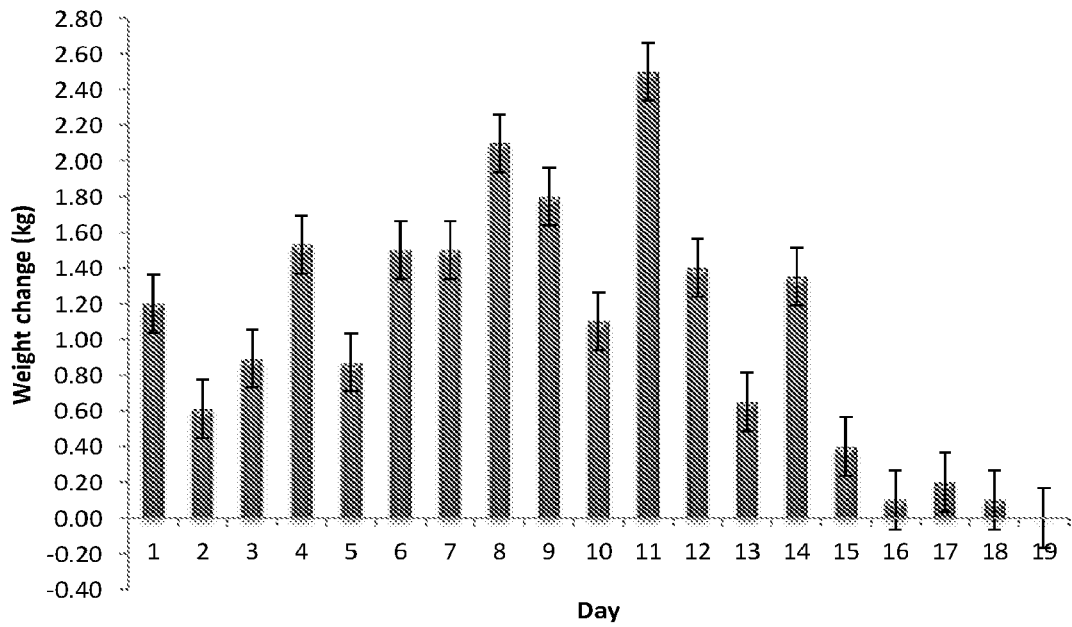
FIG. 9 depicts the mean daily change (kg) in block weight measured from day 1 of mixing unfamiliar sows into a group pen with 1×20 kg block.
Figure 10:
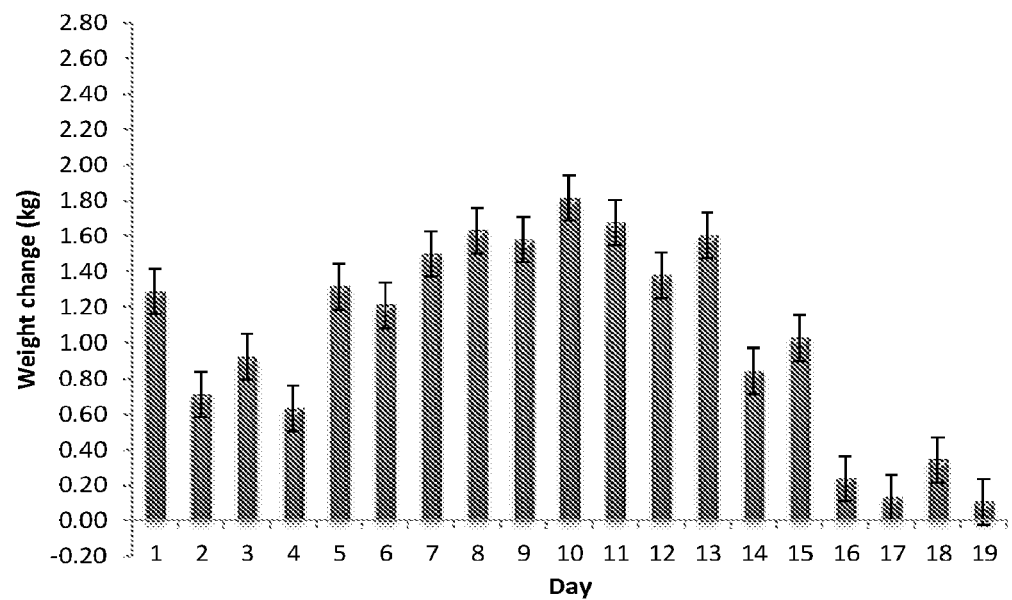
FIG. 10 depicts the mean daily change (kg) in block weight measured from day 1 of mixing unfamiliar sows into a group pen with 2×20 kg blocks.

Results revealed that mean daily change in block weight peaks after day 10 when groups of sows are housed with one supplement block (FIG. 9) and peaks after day 9 when groups of sows are housed with two supplement blocks (FIG. 10).

Figure 11:
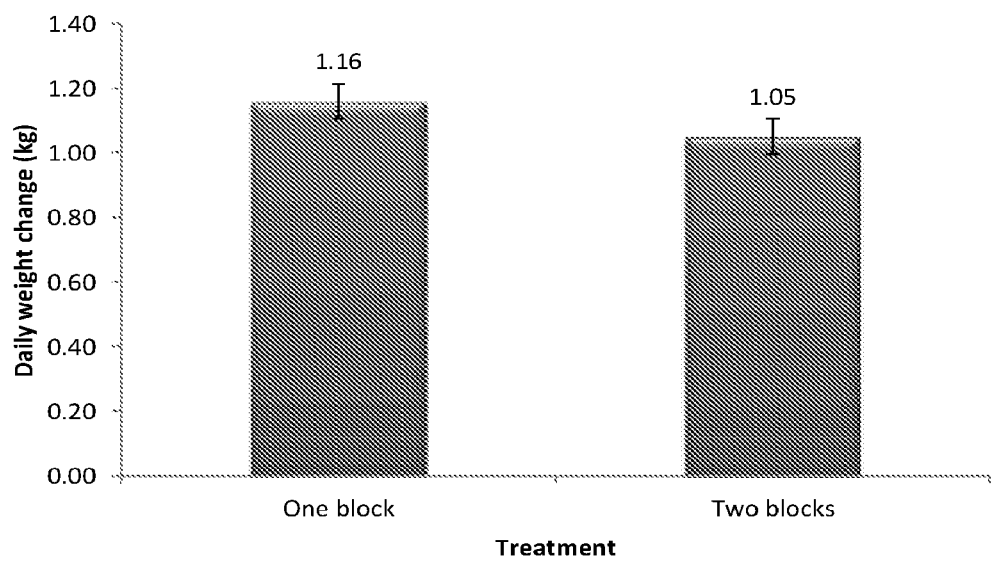
FIG. 11 depicts the mean daily change (kg) in block weight measured from day 1-19 of mixing unfamiliar sows into a group pen with either 1 or 2×20 kg block(s).

Mean daily weight change of supplement block within a pen was higher when groups of sows were housed with one block, rather than 2 blocks (FIG. 11). In a group of 14 sows, mean change in block weight was 83 g/sow for pens with one supplement block, and a combined total of 75 g/sow in pens with two supplement blocks.

Throughout this specification and the claims which follow, unless the context requires otherwise, the word "comprise", and variations such as "comprises" and "comprising", will be understood to imply the inclusion of a stated integer or step or groups of integers or steps but not the exclusion of any other integer or step or group of integers or steps.

The reference in this specification to any prior publication (or information derived from it), or to any matter which is known, is not, and should not be taken as an acknowledgement or admission or any form of suggestion that that prior publication (or information derived from it) or known matter forms part of the common general knowledge.

The invention claimed is:

1. A method of enhancing environmental enrichment of pigs, comprising providing to pigs a composition which comprises:
   a) about 40% to about 70% w/w molasses;
   b) about 10% to about 30% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
   c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
   d) about 2% to about 10% w/w of salt selected from sodium chloride and sodium nitrite; and
   e) about 13% to about 20% w/w hardening agent including both magnesium oxide and magnesium sulfate;
   wherein the composition is provided in a solid form with a hardness ranging from 2 kg/cm$^2$ to 5 kg/cm$^2$, and the percentages are based on the total weight of the composition.

2. The method according to claim 1, wherein the composition comprises:
   a) about 50% to about 60% w/w molasses;
   b) about 10% to about 20% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
   c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shark liver oil, shea nut oil, soybean oil, sunflower oil, tea seed oil, tobacco seed oil, vermonia oil, vegetable oil and wheat germ oil;
   d) about 2% to about 10% w/w of salt selected from sodium chloride and sodium nitrite; and
   e) about 13% to about 20% w/w hardening agent including both magnesium oxide and magnesium sulfate;
   wherein the composition is provided in a solid form with a hardness ranging from 2 kg/cm$^2$ to 5 kg/cm$^2$.

3. The method according to claim 1 in which the composition further comprises at least one setting agent.

4. The method according to claim 1 in which the composition is presented as a block composition.

5. The method according to claim 1 wherein the composition consists essentially of:
   a) about 40% to about 70% w/w molasses;
   b) about 10% to about 30% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
   c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite;
e) about 13% to about 20% w/w hardening agent including both magnesium oxide and magnesium sulfate; and
f) water;
wherein the composition is provided in a solid form with a hardness ranging from 2 kg/cm² to 5 kg/cm².

6. The method according to claim 1, wherein the composition consists essentially of:
a) about 50% to about 60% w/w molasses;
b) about 10% to about 20% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite; and
e) about 13% to about 20% w/w hardening agent including both magnesium oxide and magnesium sulfate; and
f) water;
wherein the composition is provided in a solid form with a hardness ranging from 2 kg/cm² to 5 kg/cm².

7. The method according to claim 1, wherein the composition consists essentially of:
a) about 40% to about 70% w/w molasses;
b) about 10% to about 30% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite;
e) about 13% to about 20% w/w hardening agent including both magnesium oxide and magnesium sulfate;
f) water; and
g) sugar;
wherein the composition is provided in a solid form with a hardness ranging from 2 kg/cm² to 5 kg/cm².

8. The method according to claim 1, wherein the composition consists essentially of:
a) about 50% to about 60% w/w molasses;
b) about 10% to about 20% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite; and
e) about 13% to about 20% w/w hardening agent including both magnesium oxide and magnesium sulfate;
f) water; and
g) sugar;
wherein the composition is provided in a solid form with a hardness ranging from 2 kg/cm² to 5 kg/cm².

9. The method according to claim 1, wherein the composition consists of:
a) about 40% to about 70% w/w molasses;
b) about 10% to about 30% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite;
e) about 13% to about 20% w/w hardening agent including both magnesium oxide and magnesium sulfate; and
f) water;
wherein the composition is provided in a solid form with a hardness ranging from 2 kg/cm² to 5 kg/cm².

10. The method according to claim 1, wherein the composition consists of:
a) about 50% to about 60% w/w molasses;
b) about 10% to about 20% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;

d) about 2% to about 10% w/w of salt selected from sodium chloride and sodium nitrite; and e) about 13% to about 20% w/w hardening agent including both magnesium oxide and magnesium sulfate; and f) water;

wherein the composition is provided in a solid form with a hardness ranging from 2 kg/cm$^2$ to 5 kg/cm$^2$.

11. The method according to claim 1, wherein the composition consists of:
a) about 40% to about 70% w/w molasses;
b) about 10% to about 30% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 5% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite;
e) about 13% to about 20% w/w hardening agent including both magnesium oxide and magnesium sulfate;
f) water; and
g) sugar;
wherein the composition is provided in a solid form with a hardness ranging from 2 kg/cm$^2$ to 5 kg/cm$^2$.

12. The method according to claim 1, wherein the composition consists of:
a) about 50% to about 60% w/w molasses;
b) about 10% to about 20% w/w insoluble fiber selected from maize, sorghum, wheat, sunflower, tomato, crucifers, peppers, potato, cotton, rice, soybean or soybean meal, sugar beet or beet pulp, sugarcane, tobacco, barley and oilseed rape;
c) about 1% to about 3% w/w triglyceride oil selected from aceituno oil, almond oil, araehis oil, babassu oil, blackcurrant seed oil, borage oil, buffalo ground oil, candlenut oil, canola oil, castor oil, coconut oil, coffee seed oil, corn oil, cottonseed oil, crambe oil, evening primrose oil, grapeseed oil, groundnut oil, hemp seed oil, kapok seed oil, linseed oil, mustard seed oil, olive oil, palm oil, palm kernel oil, peanut oil, poppy seed oil, rapeseed oil, rice bran oil, safflower oil, sesame oil, shea nut oil, soybean oil, sunflower oil, tea seed oil, tobacco seed oil, vermonia oil, vegetable oil and wheat germ oil;
d) about 2% to about 10% w/w of salt selected from sodium chloride and sodium nitrite; and
e) about 13% to about 20% w/w hardening agent including both magnesium oxide and magnesium sulfate;
f) water; and
g) sugar;
wherein the composition is provided in a solid form with a hardness ranging from 2 kg/cm$^2$ to 5 kg/cm$^2$.

13. The method according to claim 1 which involves the reduction of aggression in pigs by causing adult pigs to spend less time foraging.

14. The method according to claim 1 which involves the reduction of aggression in pigs by reducing chase behavior.

15. The method according to claim 1 which involves the reduction of aggression in pigs by reducing tail biting.

16. A method for the environmental enrichment of adult pigs which comprises the following steps:
a) mixing adult pigs in a single pen;
b) providing the pigs of step a) a set amount of feed daily once or more times per day; and
c) providing to the pigs the composition according to claim 1.

* * * * *